United States Patent
Brewer et al.

(10) Patent No.: US 9,919,096 B2
(45) Date of Patent: Mar. 20, 2018

(54) INFUSION PUMP SYSTEM AND METHOD

(71) Applicant: Bigfoot Biomedical, Inc., Milpitas, CA (US)

(72) Inventors: Tracy Brewer, Hayward, CA (US); Wenkang Qi, Cupertino, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 678 days.

(21) Appl. No.: 14/468,425

(22) Filed: Aug. 26, 2014

(65) Prior Publication Data

US 2016/0058939 A1    Mar. 3, 2016

(51) Int. Cl.
  *A61M 5/142*  (2006.01)
  *A61M 5/145*  (2006.01)
  *A61M 5/315*  (2006.01)

(52) U.S. Cl.
  CPC .... *A61M 5/14244* (2013.01); *A61M 5/14248* (2013.01); *A61M 5/14566* (2013.01); *A61M 5/31515* (2013.01); *A61M 2005/31518* (2013.01); *A61M 2205/502* (2013.01)

(58) Field of Classification Search
  CPC ......... A61M 5/14244; A61M 5/14566; A61M 5/1454; A61M 5/14248; A61M 5/31515; A61M 2005/31518; A61M 2005/14506; A61M 2205/8212
  See application file for complete search history.

(56) References Cited

U.S. PATENT DOCUMENTS

| | | |
|---|---|---|
| 4,373,527 A | 2/1983 | Fischell |
| 4,652,260 A | 3/1987 | Fenton et al. |
| 4,668,220 A | 5/1987 | Hawrylenko |
| 4,902,278 A | 2/1990 | Maget et al. |
| 5,062,830 A * | 11/1991 | Dunlap .................. A61M 5/30 604/68 |
| 5,176,632 A | 1/1993 | Bernardi |
| 5,637,095 A | 6/1997 | Nason et al. |
| 5,672,167 A | 9/1997 | Athayde et al. |
| 5,718,562 A | 2/1998 | Lawless |
| 5,800,420 A | 9/1998 | Grose et al. |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

International Search Report and Written Opinion in International Application No. PCT/US2015/46763, dated Jan. 11, 2016, 8 pages.

(Continued)

*Primary Examiner* — Bhisma Mehta
*Assistant Examiner* — Jenna Zhang
(74) *Attorney, Agent, or Firm* — Fish & Richardson P.C.

(57) ABSTRACT

Some embodiments of an infusion pump system include a pump device with a drive system that is configured to attach with a medicine cartridge in manner that reduces the likelihood of dosage inaccuracies. In one example, the drive system of the pump device can be equipped with a plunger engagement device that is configured to mechanically anchor into a plunger of the medicine cartridge, and then to bias the plunger of the medicine cartridge in a direction toward a piston rod of the drive system.

21 Claims, 10 Drawing Sheets

(56) References Cited

U.S. PATENT DOCUMENTS

| | | |
|---|---|---|
| 6,106,498 A | 8/2000 | Friedli |
| 6,127,061 A | 10/2000 | Shun et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,491,684 B1 | 12/2002 | Joshi et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,537,268 B1 | 3/2003 | Gibson et al. |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,668 B1 | 12/2003 | Kleeman et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,957 B2 | 9/2004 | Carpenter et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,936,032 B1 | 8/2005 | Bush et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,232,423 B2 | 6/2007 | Mernoe et al. |
| 7,597,682 B2 | 10/2009 | Moberg |
| 7,654,982 B2 | 2/2010 | Carlisle et al. |
| 7,875,022 B2 | 1/2011 | Wenger et al. |
| 2001/0041869 A1 | 11/2001 | Causey, III et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0016568 A1 | 2/2002 | Lebel |
| 2002/0032402 A1 | 3/2002 | Daoud et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0156462 A1 | 10/2002 | Stultz |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0105430 A1* | 6/2003 | Lavi ............ A61M 5/2033 604/136 |
| 2003/0125672 A1 | 7/2003 | Adair et al. |
| 2003/0161744 A1 | 8/2003 | Vilks et al. |
| 2003/0199825 A1 | 10/2003 | Flaherty |
| 2003/0216683 A1* | 11/2003 | Shekalim ............ A61M 5/1454 604/67 |
| 2003/0216686 A1 | 11/2003 | Lynch et al. |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |

(56) References Cited

U.S. PATENT DOCUMENTS

| | | |
|---|---|---|
| 2004/0127844 A1 | 7/2004 | Flaherty |
| 2004/0153032 A1 | 8/2004 | Garnbotto et al. |
| 2004/0171983 A1 | 9/2004 | Sparks et al. |
| 2004/0176727 A1 | 9/2004 | Shekalim |
| 2004/0187952 A1 | 9/2004 | Jones |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0038332 A1 | 2/2005 | Saidara et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0113745 A1 | 5/2005 | Stultz |
| 2005/0124866 A1 | 6/2005 | Elaz et al. |
| 2005/0160858 A1 | 7/2005 | Mernoe |
| 2005/0171476 A1* | 8/2005 | Judson ............ A61M 5/14566 604/131 |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245878 A1 | 11/2005 | Mernoe et al. |
| 2005/0251097 A1* | 11/2005 | Mernoe ............ A61M 5/14244 604/221 |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1* | 7/2006 | Imhof ............ A61M 5/14566 222/390 |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2006/0247582 A1* | 11/2006 | Alheidt ............ A61M 5/31515 604/228 |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0093750 A1 | 4/2007 | Jan et al. |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1* | 7/2007 | Causey ............ A61M 5/14244 604/131 |
| 2007/0197968 A1* | 8/2007 | Pongpairochana ..... A61M 5/20 604/131 |
| 2007/0251097 A1* | 11/2007 | Terry ............ A47G 21/02 30/123 |
| 2008/0009824 A1 | 1/2008 | Moberg et al. |
| 2008/0208627 A1 | 8/2008 | Skyggebjerg |
| 2008/0294094 A1* | 11/2008 | Mhatre ............ A61M 5/1413 604/65 |
| 2008/0294142 A1* | 11/2008 | Patel ............ A61M 5/1413 604/506 |
| 2009/0318878 A1* | 12/2009 | Chavez ............ A61M 5/20 604/208 |
| 2010/0325864 A1 | 12/2010 | Briones et al. |
| 2012/0078170 A1 | 3/2012 | Smith et al. |
| 2012/0330270 A1 | 12/2012 | Colton |
| 2013/0046276 A1* | 2/2013 | Mernoe ............ A61M 5/14244 604/500 |
| 2014/0121633 A1 | 5/2014 | Causey et al. |

FOREIGN PATENT DOCUMENTS

| | | |
|---|---|---|
| DE | 102 36 669 | 2/2004 |
| EP | 0 062 974 | 10/1982 |
| EP | 0 275 213 | 7/1988 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| JP | A 9-504974 | 5/1997 |
| JP | 2000-513974 | 10/2000 |
| JP | 2002-507459 | 3/2002 |
| JP | A 2002-523149 | 7/2002 |
| WO | WO 90/15928 | 12/1990 |
| WO | WO 97/21457 | 6/1997 |
| WO | WO 1998/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 2001/054753 | 8/2001 |
| WO | WO 2001/72360 | 10/2001 |
| WO | WO 2001/91822 | 12/2001 |
| WO | WO 2001/91833 | 12/2001 |
| WO | WO 2002/40083 | 5/2002 |
| WO | WO 2002/057627 | 7/2002 |
| WO | WO 2002/068015 | 9/2002 |
| WO | WO 2002/084336 | 10/2002 |
| WO | WO 2002/100469 | 12/2002 |
| WO | WO 2003/026726 | 4/2003 |
| WO | WO 2003/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |

OTHER PUBLICATIONS

Accu-Chek Spirit, "Pump Therapy Made for You," Roche, 2006, 6 pages.

Asante Solutions Pearl User Manual, Asante Inc., 2012, 180 pages.

Collins and Lee, "Microfluidic flow transducer based on the measurement of electrical admittance," *Lab Chip*, 2004 4 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

OmniPod Insulin Management System-Investor Relations—Press Release, Feb. 1, 2005, http://investors.insulet.com/phoenix.zhtml?c=209336&p=iro-newsArticleID=9887088&highlight= 1 page.

(56) References Cited

OTHER PUBLICATIONS

OmniPod Quick Start Guide, 2007, 2 pages.
Patent Abstracts of Japan, vol. 1999, No. 04, and JP 11 010036 , Apr. 30, 1999 and Jan. 19, 1999, Toray Ind. Inc.
The Medtronic Diabetes Connection, 2006, 6 pages.
Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

* cited by examiner

INFUSION PUMP SYSTEM AND METHOD

TECHNICAL FIELD

This document relates to an infusion pump system, such as a portable infusion pump system for dispensing a medicine.

BACKGROUND

Pump systems are commonly used to deliver one or more fluids to a targeted individual. For example, a medical infusion pump system may be used to deliver a medicine to a patient as part of a medical treatment. The medicine that is delivered by the infusion pump system can depend on the condition of the patient and the desired treatment plan. For example, infusion pump systems have been used to deliver insulin to the vasculature of diabetes patients so as to regulate blood-glucose levels.

Infusion pump systems often need to deliver medicine in accurately controlled dosages. Over-dosages and under-dosages of medicine can be detrimental to patients. For example, an infusion pump system that delivers an over-dosage or under-dosage of insulin to a diabetes patient can significantly affect the blood-glucose level of the patient.

SUMMARY

Some embodiments of an infusion pump system include a pump device with a drive system that is configured to attach with a medicine cartridge in manner that reduces the likelihood of dosage inaccuracies. For example, in particular embodiments, the drive system of the pump device can be equipped with a plunger engagement device that is configured to mechanically anchor into a plunger of the medicine cartridge, and then to bias the plunger of the medicine cartridge in a direction toward a piston rod of the drive system. In such circumstances, the plunger engagement device can reduce or eliminate a gap that might otherwise be present between a rearward face of the plunger and the forward face of the pushing element of the drive system, and can and thereafter retaining the plunger in a predictable position relative to the piston rod during operation of the pump device.

Particular embodiments described herein include a portable infusion pump system. The system may include a pump housing that defines a space to receive a medicine cartridge, and a drive system to dispense medicine from the medicine cartridge when the medicine cartridge is received by the pump housing. The drive system may include a piston rod configured to forwardly advance toward the medicine cartridge when the medicine cartridge is received by the pump housing, and a plunger engagement device coupled to the piston rod. The plunger engagement device may include at least one penetration member to couple the drive system to a plunger of the medicine cartridge. Optionally, the plunger engagement device may also include a spring adjustable from a deactivated condition to an activated condition in which a spring force of the spring biases the plunger towards the piston rod.

In other embodiments, a portable infusion pump system may include a pump housing that defines a space to receive a medicine cartridge, a drive system to dispense medicine from the medicine cartridge when the medicine cartridge is received by the pump housing, and a controller device. Optionally, the drive system may include a piston rod configured to forwardly advance toward the medicine cartridge when the medicine cartridge is received by the pump housing, and a plunger engagement device coupled to the piston rod. Optionally, the controller device may be in the form of a device that is removably attachable to the pump housing so as to electrically connect with a pump device comprising the pump housing and the drive system. The controller device may house control circuitry configured to communicate with the drive system positioned in the pump housing to control dispensation of the medicine from the pump device. The plunger engagement device may include a piston hub coupled to the piston rod, a retention plate installed about the piston hub, and at least one penetration member supported by the retention plate to couple the drive system to a plunger of the medicine cartridge. Also, the plunger engagement device may optionally include a spring seated between the piston hub and the retention plate. The spring may be adjustable from a deactivated condition to an activated condition in which a spring force of the spring biases the retention plate away from the piston hub to pull the plunger against a surface of the piston hub.

In some embodiments of a portable infusion pump system, the system may include a pump housing and a drive system that includes a plunger engagement device. The pump housing may define a space to receive a medicine cartridge. The drive system may be configured to dispense medicine from the medicine cartridge when the medicine cartridge is received by the pump housing. The drive system may include a piston rod configured to forwardly advance toward the medicine cartridge when the medicine cartridge is received by the pump housing, and the plunger engagement device coupled to the piston rod. The plunger engagement device may include at least one means for penetrating a plunger of the medicine cartridge, and a means for biasing the plunger towards the piston rod by adjusting from a deactivated condition to an activated condition. Optionally, the means for biasing may include a spring device.

Particular embodiments described herein include a method of operating an infusion pump device. The method may include receiving a medicine cartridge in an internal space of a housing of a pump device. A plunger engagement device may be positioned in the internal space. The method may also include penetrating a plunger of the medicine cartridge with at least one penetration member of the plunger engagement device. Optionally, the method may further include, after penetrating the plunger with said at least one penetration member, applying a spring bias to the plunger to bias the plunger towards a component of a drive system of the pump device.

Some or all of the embodiments described herein may provide one or more of the following advantages. First, some embodiments of the drive system of the pump device can accurately and incrementally dispense fluid from the pump device in a controlled manner. For example, the drive system housed within the pump device can include a plunger engagement device (positioned at the leading end of the piston rod) that attaches to a plunger of a medicine cartridge installed into the pump device, and plunger engagement device can be configured to reduce or eliminate any gap between the piston rod and the plunger (e.g., a gap that is a potential source of inaccuracy in the dispensation of the medicine). Accordingly, in particular circumstances, the plunger engagement device may reduce the likelihood of dosage inaccuracy of the infusion pump device by inhibiting inadvertent movement of the plunger relative to the piston rod.

Second, in particular embodiments, the pump device may be removably attached to a controller device so that a user can readily monitor infusion pump operation by simply viewing a user interface that is releasably connected to the pump device.

Third, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DETAILED DESCRIPTION OF ILLUSTRATIVE EMBODIMENTS

Figure 1:
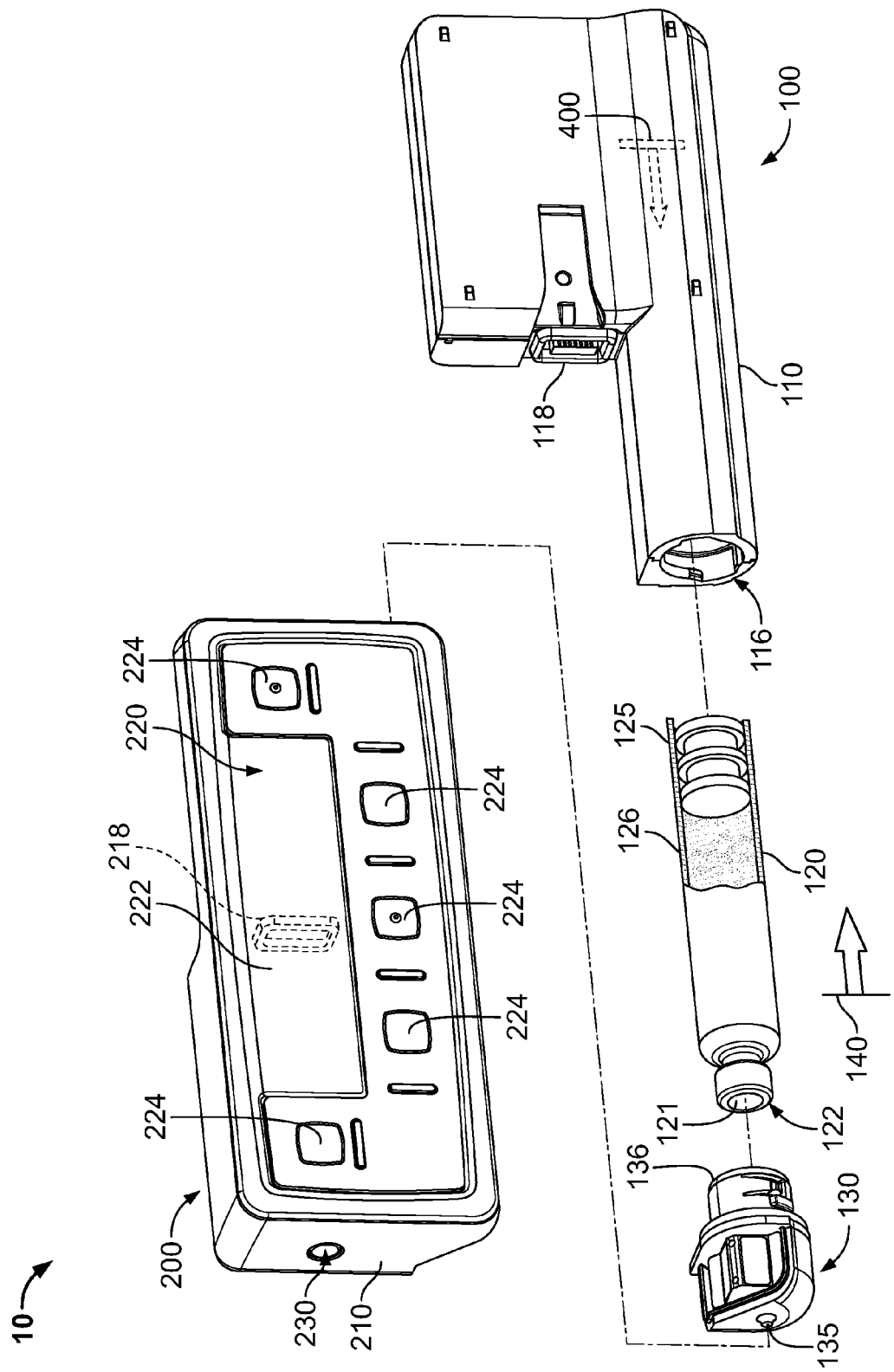
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing 110 that defines a cavity 116 in which a fluid cartridge 120 can be received. The pump device 100 further includes a cap device 130 to retain the fluid cartridge 120 in the cavity 116 of the housing 110. The pump device 100 can include a drive system 300 (FIG. 3) that advances a plunger 125 in the fluid cartridge 120 so as to dispense fluid 126 therefrom. The drive system 300 of the pump device can be equipped with a plunger engagement device 400, which is positioned within the cavity 116 and is configured to attach with the plunger 125 upon inserted of the cartridge 120 into the cavity. For example, as described in more detail below in connection with FIGS. 5A-8C, the plunger engagement device 400 can be configured to initially secure to the plunger 125 (e.g., with one or more penetration members that anchor into the plunger 125) and then to bias the plunger 125 in a rearward direction that reduces or eliminates a gap (which might otherwise cause inaccuracy in dispensation dosages) between the rearward face of the plunger 125 and a forward driving face of the drive system 300.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device (and drive system therein) is employed with each new fluid cartridge.

Briefly, in use, the pump device 100 is configured to removably attach to the controller device 200 in a manner that provides a secure fitting, an overall compact size, and a reliable electrical connection that is resistant to water migration. For example, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 2). Moreover, at least one of the pump device 100 or the controller device 200 can include a release member that facilitates an easy-to-use detachment and replacement process.

The pump system 10 can be a medical infusion pump system that is configured to controllably dispense a medicine from the fluid cartridge 120. As such, the fluid 126 contained in the fluid cartridge 120 can include a medicine to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Byetta®, Symlin®, or others). Such a fluid cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, antiemetics, osteoporosis treatments, or other injectable medicines. The fluid cartridge 120 may have other configurations. For example, the fluid cartridge 120 may comprise a reservoir that is integral with the pump housing 110 (e.g., the fluid cartridge 120 can be defined by one or more walls of the pump housing 110 that surround a plunger to define a reservoir in which the medicine is injected or otherwise received).

In some embodiments, the pump device 100 can include one or more structures that interfere with the removal of the fluid cartridge 120 after the fluid cartridge 120 is inserted into the cavity 116. For example, the pump housing 110 can include one or more retainer wings (not shown in FIG. 1) that at least partially extend into the cavity 116 to engage a portion of the fluid cartridge 120 when the fluid cartridge 120 is installed therein. Such a configuration may facilitate the "one-time-use" feature of the pump device 100. In some embodiments, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversible attach to the pump housing 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system of the pump device 100. As described in more detail below, the pump device 100 can include a drive system 300 (FIG. 3) that causes controlled dispensation of the medicine or other fluid from the fluid cartridge 120. In some embodiments, the drive system 300 incrementally advances a piston rod 370 (refer to FIG. 3) longitudinally into the fluid cartridge 120 so that the fluid is forced out of its output end 122. A septum 121 at the output end 122 of the fluid cartridge 120 can be pierced to permit fluid outflow when the cap device 130 is coupled to the pump housing 110. For example, the cap device 130 may include a penetration needle (not shown) that punctures the septum 121 during engagement of the cap device 130 with the housing 110, which creates a fluid path to an output port 135 of the cap device 130.

In some embodiments, a longitudinal force 140 is applied to the fluid cartridge 120 as various components of the pump device 100 are prepared for use by a user. For example, in some embodiments, the longitudinal force 140 may be applied by a user's fingers as the fluid cartridge 120 is inserted into the pump housing 110 (e.g., the user may press the fluid cartridge 120 longitudinally into the cavity). In some embodiments, the longitudinal force 140 may be applied during engagement of the cap device 130 with the housing 110. For example, one or more actions by a user to engage the cap device 130 with the housing 110 (e.g., pressing down on a portion of the cap device 130 or rotating a portion of the cap device 130) may cause a shoulder surface 136 of the cap device 130 to bear against a flange surface 129 of the fluid cartridge 120. In some embodiments, the longitudinal force 140 can be applied in stages. For example, a first stage of the longitudinal force 140 may be applied from the user's fingers as the fluid cartridge 120 is inserted into the pump housing 110, and a second stage of the longitudinal force 140 may be applied from the cap device 130 pressing upon the cartridge 120 during engagement of the cap device 130.

Still referring to FIG. 1, in some embodiments, the longitudinal force 140 causes the plunger 125 to be secured to the plunger engagement device 400 of the piston rod 370. For example, the longitudinal force 140 may drive the fluid cartridge 120 rearward (relative to the housing 110) toward one or more penetration members 436 (refer also to FIG. 7) of the plunger engagement device 400. In such circumstances, the penetration members 436 may penetrate into the plunger 125 and thereby secure the fluid cartridge 120 to the piston rod 370 (FIG. 8A). Preferably, this initial component of the longitudinal force 140 (causing the plunger engagement device 400 to penetrate into the plunger 125) is accomplished when the user applies an insertion force with his or her fingers to insert the cartridge 120 into the cavity 116 (prior to attaching the cap device 130). Then, when the cap device 130 is mounted to the pump housing 110, the septum 121 of the cartridge 120 is pierced by the penetration needle of the cap device 130, as described above. As previously described, the cap device 130 then applies a second component of the longitudinal force 140 that can further urge the cartridge device 120 rearwardly into the cavity 116. In some embodiments, the component of the longitudinal force 140 applied by the cap device 130 upon the cartridge 120 provides a "break away" force, initiating movement of the plunger 125 to dispense a small amount of medicine from the infusion pump device 100. This small amount of dispensation may at least partially prime a flexible tube 147 (FIG. 2) that delivers the medicine to an infusion site. As described in more detail below in connection with FIGS. 4-8C, in some embodiments, the longitudinal force 140 (e.g., the initial component or the second component) may cause the activation of a retention spring 406 (FIGS. 5A-5B) of the plunger engagement device 400. Once activated, the retention spring 406 urges the plunger 125 towards the piston rod 370 (refer to FIG. 8C), which can reduce or eliminate any gap that may be present between the plunger 125 and the front drive face of the piston rod 370 (e.g., a gap that might otherwise cause an inaccuracy in the dispensation dosages of the medicine). Thus, the plunger engagement device 400 may reduce the likelihood of dosage inaccuracy of the infusion pump device 100 by inhibiting inadvertent movement of the plunger 125 relative to the piston rod 370.

When the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the fluid cartridge 120. Power signals, such as signals from a rechargeable battery (not shown) of the controller device 200 and from the power source 310 (refer to FIG. 3) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector 218 on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the power source 310 to the controller device 200, where the signals may be used to charge the rechargeable battery or to power components of the controller device 200. Additionally or alternatively, the electrical connectors 118 and 218 may facilitate transmission of one or more power signals from the rechargeable battery of the controller device 200 to the pump device 100, where the signals may be used to provide power to components of the pump device 100.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas. The inspection light device 230 can also be used to notify the user to an alert condition of the pump system 10. An activation of the inspection light device 230 can thereby provide a visual notification (as an alternative to, or in addition to, the visual notification provided on the display device 222) to the user that attention to the pump system 10 is warranted.

When the infusion pump system 10 operates, the controller device 200 can be removably attached to the pump device 100 in a side-by-side arrangement. For example, the pump device 100 may be moved in a longitudinal direction toward the controller device 200 until the complementary features connect and secure the separate components in the side-by-side arrangement. The controller device 200 can include a controller housing 210 having a number of features that are configured to mate with complementary features of the pump housing 110 so as to form a releasable mechanical connection.

Figure 2:
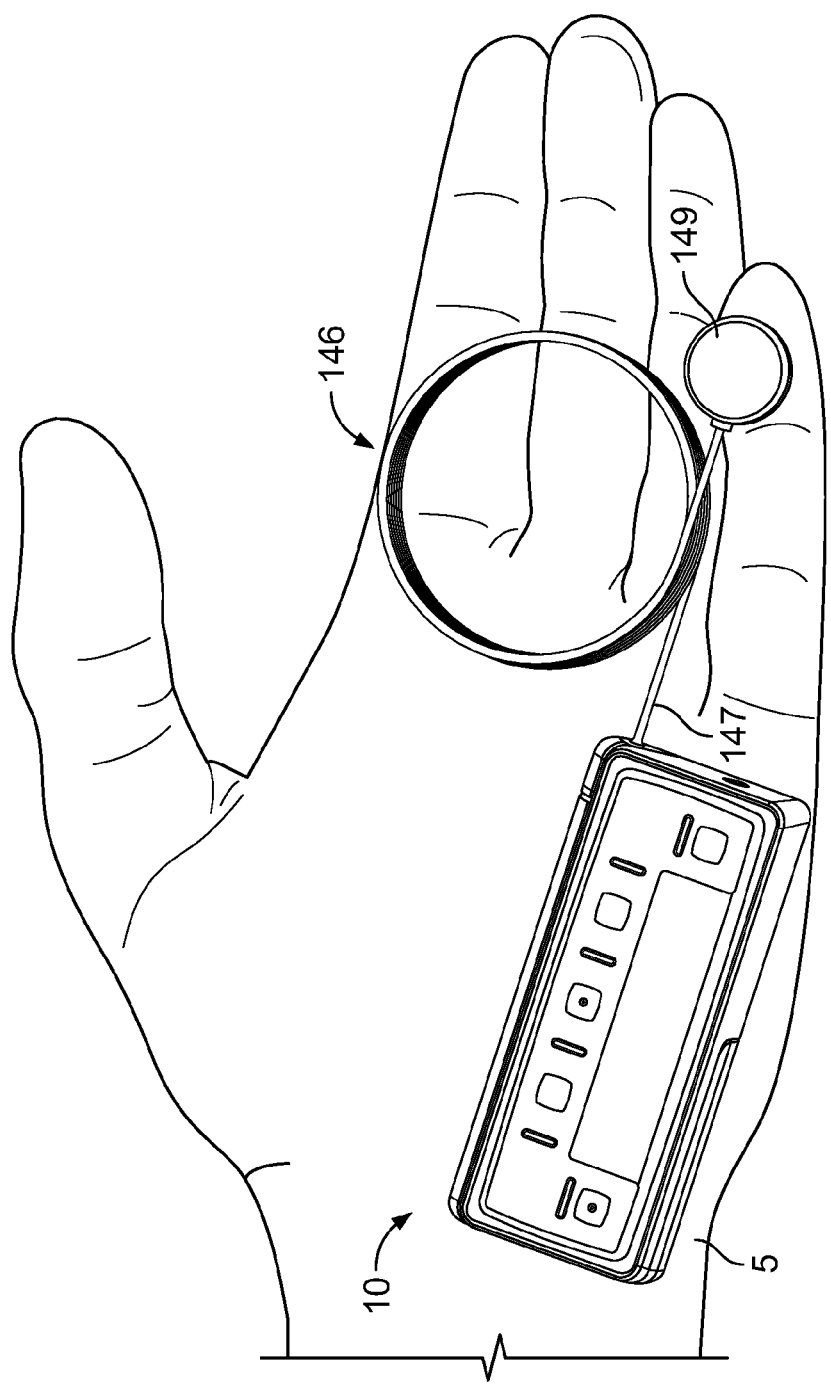
FIG. 2 is a perspective view of an infusion pump system, in accordance with some embodiments.

Referring to FIG. 2, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 2 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 1) of the fluid cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Figure 3:
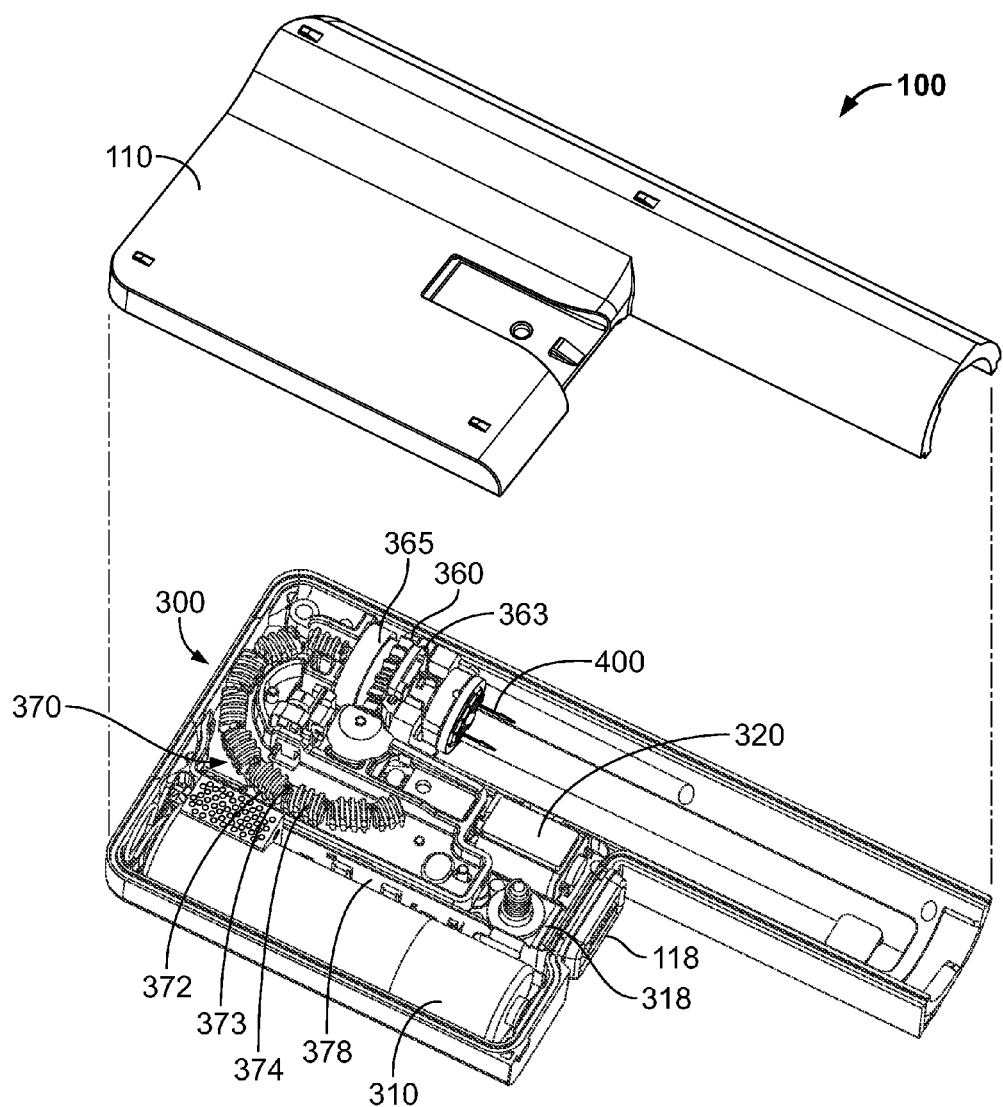
FIG. 3 is an exploded perspective view of a pump device of the infusion pump system of FIG. 1.

Referring now to FIG. 3, the drive system 300 of the pump device 100 in this embodiment is controlled by the controller device 200 (FIG. 1). As described in more detail below, the drive system 300 can incrementally dispense fluid in a controlled manner from fluid cartridge 120 inserted into the pump device 100. Also, the pump device 100 may include a connector circuit 318 to facilitate the transfer of signals to and from the electrical connector 118. In some implementations, the connector circuit 318 in the pump device 100 may include a memory device that can store data regarding the pump device 100 and its operational history. As previously described, the electrical connector 118 of the pump device 100 can mate with the connector 218 of the controller device 200 so that electrical communication can occur between the pump device 100 and the controller device 200. In some embodiments, the connector circuit 318 can operate as a passageway to transmit electrical control signals from the controller circuitry of the controller device 200 to the drive system 300. The connector circuit 318 can also operate as a passageway for the electrical power from a power source 310 housed in the pump device 100 to pass to the controller device 200 for recharging of the rechargeable battery. Furthermore, the connector circuit 318 can operate as a passageway for feedback signals from the drive system 300 to the controller circuitry of the controller device 200.

In this embodiment, the housing 110 of pump device 100 carries the drive system 300 and the power source 310. For example, the power source 310 may comprise an alkaline battery cell, such as a 1.5 Volt "AAA" alkaline battery cell, which is contained in a dedicated space of the pump housing 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack of the controller device 200 when the pump device 100 is attached to the controller device 200. In some embodiments, the power source 310 is used to provide energy to the drive system 300 of the pump device 100 (in response to control signals from the controller device 200), and also to electronic components of the controller device 200. In particular embodiments, the power source 310 may provide the energy to power all aspects of the infusion pump system 10. In some alternative embodiments, the rechargeable battery housed in the controller device 200 may provide the energy to power all aspects of the infusion pump system 10. In other embodiments, the rechargeable battery of the controller device 200 and the power source 310 may each be responsible for powering particular aspects of the infusion pump system 10. In further embodiments, the rechargeable battery may provide the energy to supplement the energy provided by the power source 310 to power aspects of the infusion pump system.

Still referring to FIG. 3, in some embodiments, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 400. The flexible piston rod 370 comprises a plurality of segments 372 serially connected by hinge portions 373 so that the flexible piston rod 370 is adjustable from a curved shape to a noncurved shape. The plurality of segments 372 and the interconnecting hinge portions 373 can be integrally formed in one piece from one or more moldable materials (e.g., polymer materials such as Nylon or POM). In this embodiment, each of the plurality of rod segments 372 includes an exterior thread pattern 374 along at least one cylindrical surface portion. The plunger engagement device 400 is arranged at a forward end of the piston rod 370. As such, the plunger engagement device 400 faces toward the fluid cartridge 120 when the fluid cartridge 120 is inserted into the cavity 116.

The flexible piston rod 370 can be incrementally advanced forward (toward the fluid cartridge 120) so as to dispense the medicine from the pump device 100 by pressing against the plunger 125. The force from the piston rod 370 overcomes a frictional "glide force" of the plunger 125 to advance the plunger 125 through the fluid cartridge 120 to dispense medicine. In this embodiment, the reversible motor 320 drives a gear system (not shown in FIG. 3, but described in U.S. Pat. No. 8,409,142, the entirety of which is incorporated by referenced herein) to cause the rotation of the drive wheel 360 that is coupled with the bearing 365. The drive wheel 360 may include a central aperture with an internal thread pattern, which mates with the external thread pattern 374 of the rod segments 372. The interface of the threaded portions of the drive wheel 360 and rod segments 372 of the flexible piston rod 370 may be used to transmit force from the drive wheel 360 to the piston rod 370. Accordingly, in the embodiment of FIG. 3, the drive wheel 360 is the driver while the flexible piston rod 370 is the driven member. Thus, the rotation of the drive wheel 360 can incrementally drive the flexible piston rod 370 forward in a linear longitudinal direction to dispense medicine. In some embodiments, drive wheel 360 can advance the piston rod 370 a longitudinal distance of about 16 microns or less (e.g., about 4 microns to about 12 microns, about 5 microns to about 9 microns, or about 6 microns to about 8 microns) for each incremental motion cycle of the gear system. The controller device 200 can communicate control signals to the drive system 300 or other components of the pump device 100 to regulate the incremental movement of the piston rod 370 based on a specific dosage of medicine.

Figure 4:
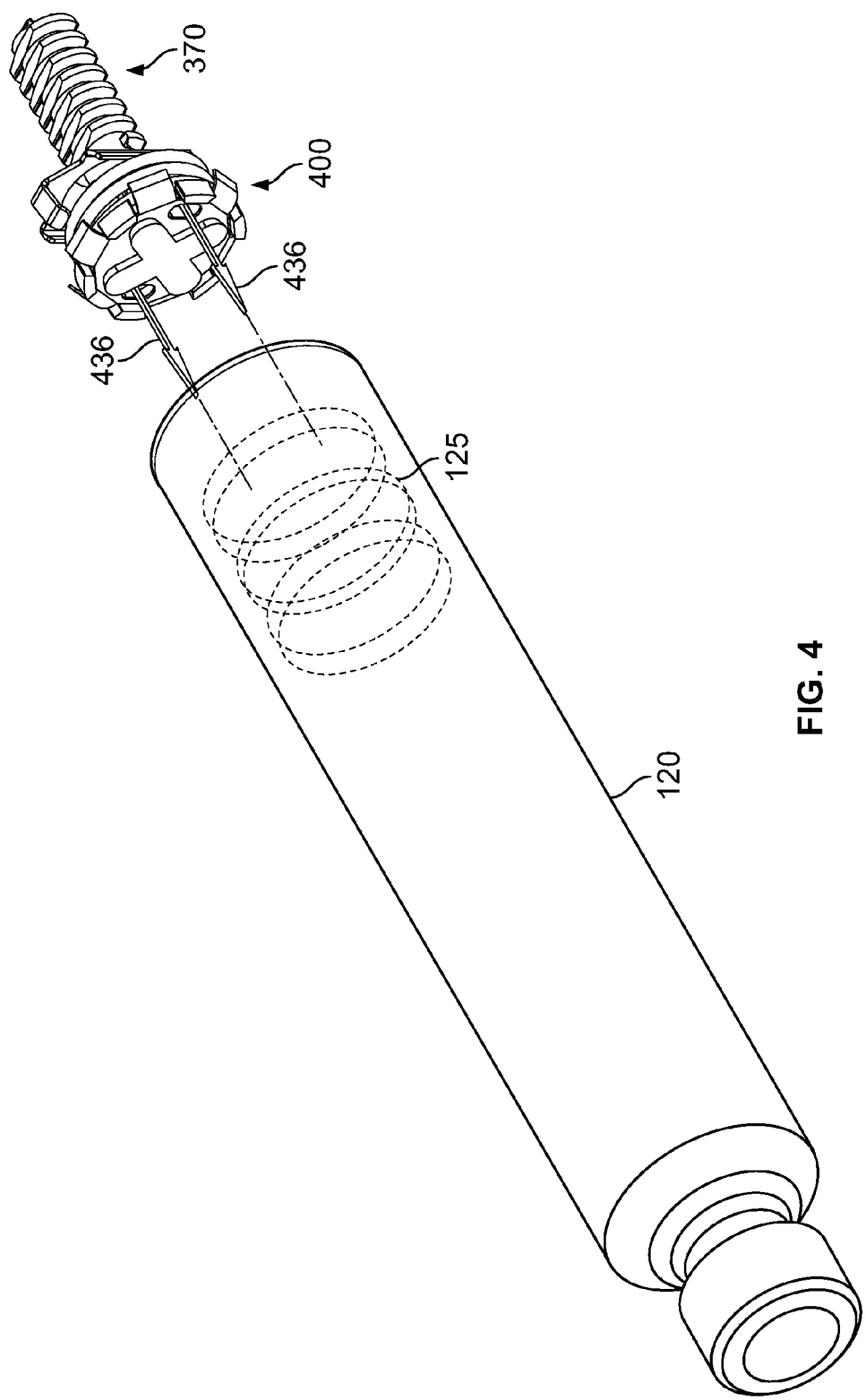
FIG. 4 is an exploded perspective view of a plunger engagement device and a fluid cartridge of the infusion pump system of FIG. 1.
Figure 8A:
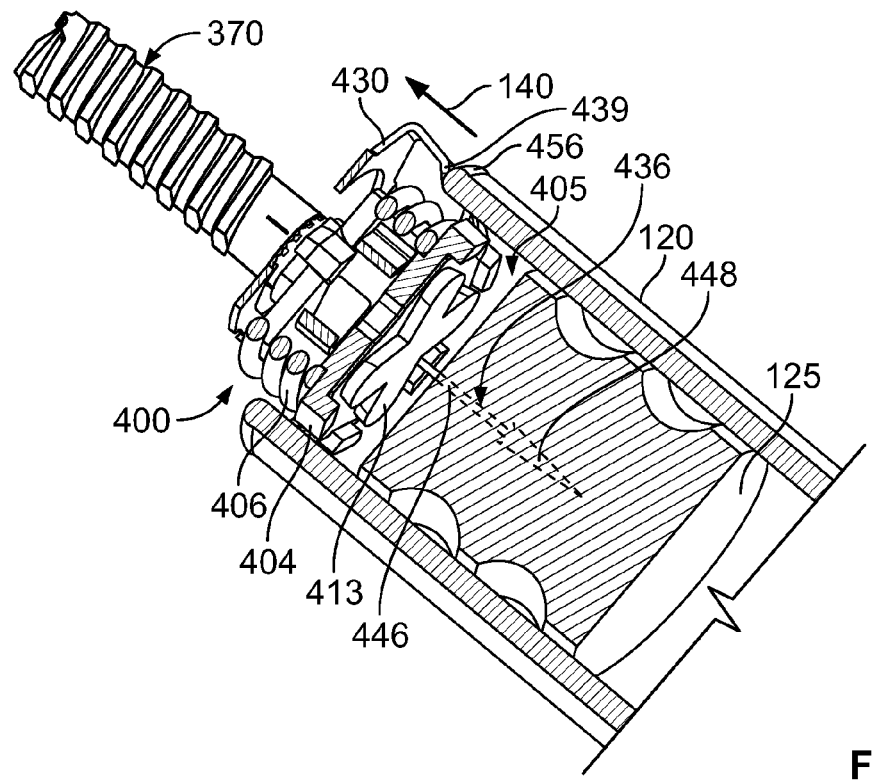
FIGS. 8A-C are progressive perspective views of the plunger engagement device and the fluid cartridge of FIG. 4.
Figure 8B:
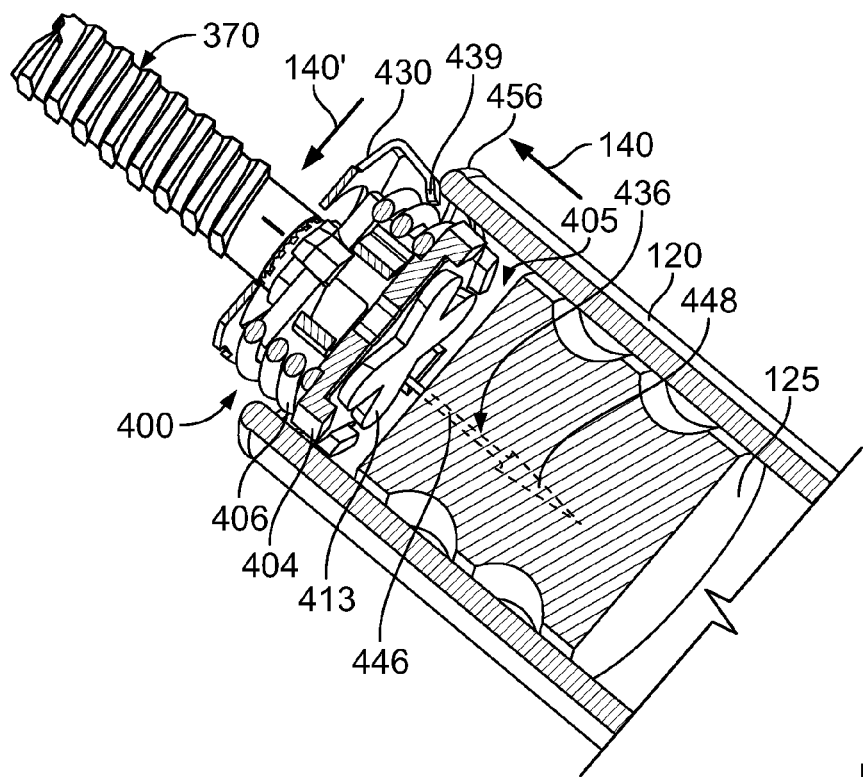
Figure 8C:
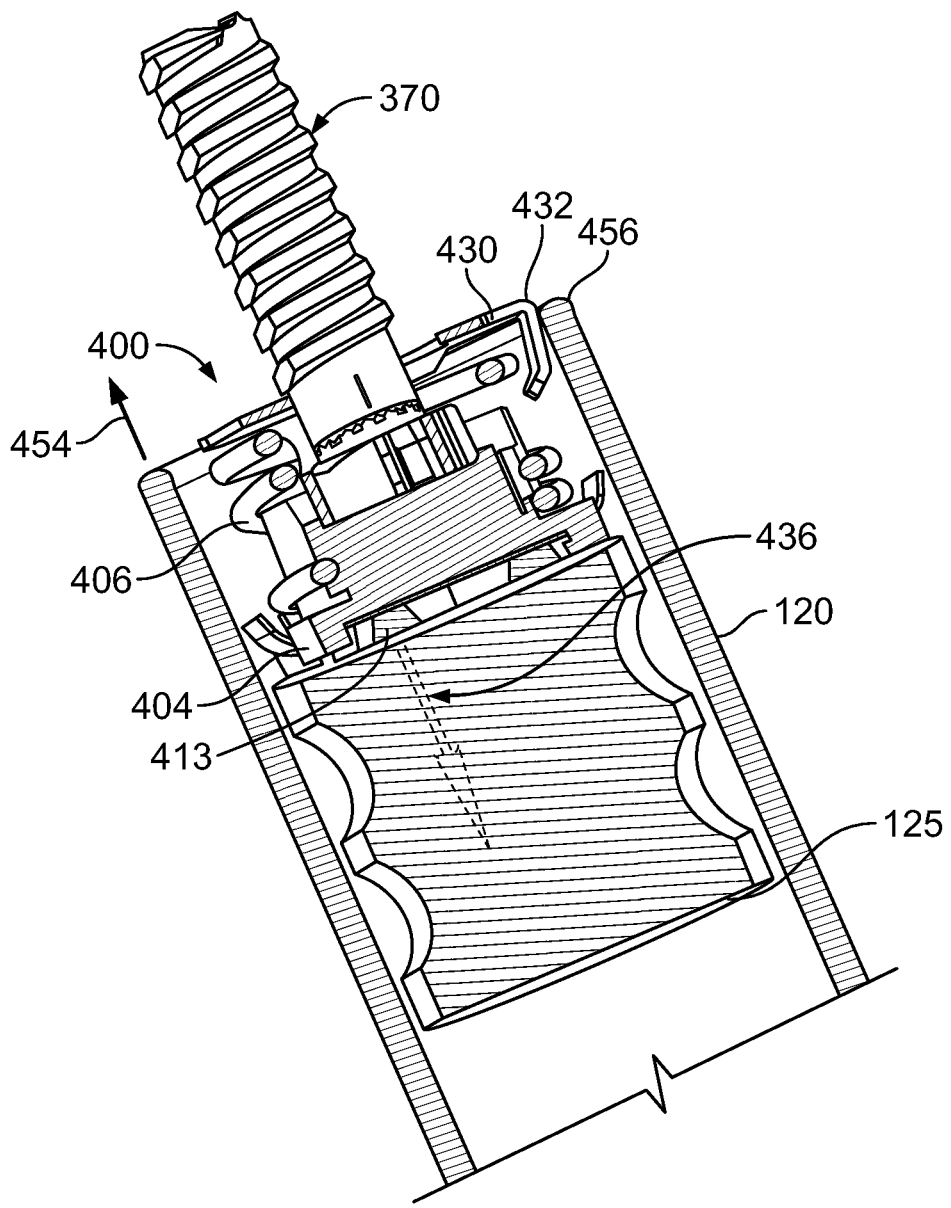

Referring now to FIG. 4, the plunger engagement device 400 can attach to the plunger 125 of the fluid cartridge 120 when the two components are urged together. For example, as previously described in connection with FIG. 1, a longitudinal force 140 may be applied to the fluid cartridge 120 during insertion of the fluid cartridge 120 into the cavity 116 (applied via the user's fingers) and/or during engagement of the cap device 130 to the pump housing 110. This longitudinal force 140 can urge the fluid cartridge 120 (and the plunger 125 therein) toward the plunger engagement device 400. In this embodiment, the plunger engagement device 400 includes a plurality of penetration members 436 that extend toward the plunger 125 and are configured to penetrate into the plunger 125 in response to the longitudinal force 140 (FIGS. 8A-C). Thereafter, the plunger 125 may remain coupled to the piston rod 370 via that plunger engagement device 400 during operation of the pump device 100. As described below, the penetration members 436 may be in the form of anchor barbs that hold the plunger 125 (and thus the cartridge 120) inside the cavity 116 with a retention force that hinders removal of the cartridge 120 from the cavity 116 (and thereby hinders attempts to reuse the one-time-use pump device 100 in this embodiment).

Under certain circumstances, other stresses exerted on the plunger 125 may overcome the retention force of the penetration members 436, causing the plunger 125 to not fully seat against the forward face of the piston rod 370 (e.g., the face of a pusher block 413 as shown in FIG. 8A) or to move away from piston rod 370 through the fluid cartridge 120. In such circumstances, a gap 405 may be present between the rearward face of the plunger 125 and the forward face of the piston rod 370 (refer, for example, to FIG. 8A). As described in more detail below, such a gap may be the source of inaccuracy in dosage dispensations from the pump device 100 (e.g., the piston rod 370 might advance forward, but the plunger 125 might not advance the same amount forward). Additionally, in some cases in which the plunger 125 moves relative to the plunger 125 after engagement, this movement of the plunger 125 may cause some fluid 126 to be unintentionally dispensed. Such other stresses exerted on the plunger 125 can be caused, for example, by material creep, thermal shock, elastic recovery of the elastomeric material of the plunger, and/or an impact force (e.g., if the pump device 100 is dropped on the ground). As yet another example, when there is a pressure differential between the interior and exterior of the pump device 100, in some circumstances the plunger 125 can be biased to pull away from the piston rod 370 by a small amount.

As previously described, the gap between the plunger 125 and the piston hub 404 may cause dosage inaccuracies during operation of the pump device 100. For example, the piston rod 370 may be driven forward through a longitudinal distance equal to the size of the gap before the piston hub 404 contacts the plunger 125 to push the plunger 125 through the fluid cartridge 120. In this case, the piston rod 370 moves a greater distance through the fluid cartridge 120 than the plunger 125, which may result in an inaccurate dispensation of medicine (an under-dosage in this particular example).

An inaccurate dosage of medicine (e.g., more or less medicine than the dosage determined by the controller device 200) may be dispensed if the movement of the plunger 125 does not closely match the incremental movement to the piston rod 370. As noted above, in this embodiment, the incremental motion of the piston rod 370 and plunger 125 required to dispense an appropriate dose of medicine from the fluid cartridge 120 may be 16 microns or less. Therefore, a small gap between the between the rearward face of the plunger 125 and the forward face of the piston rod (even a gap as small as about 6 microns to about 8 microns) could potentially cause a dosage inaccuracy along the order of one or more dispensation cycles of the drive system. Thus, in some embodiments, the plunger engagement device 400 is provided with a retention spring 406 (FIGS. 5A and 5B) to increase the dosage accuracy of the infusion pump device 100 by reducing or eliminating any such gap and by inhibiting inadvertent movement of the plunger 125 relative to the piston rod 370. As described below, once activated, the retention spring 406 perpetually urges the plunger 125 against the piston hub 404 to resist any peripheral forces.

Figure 5A:
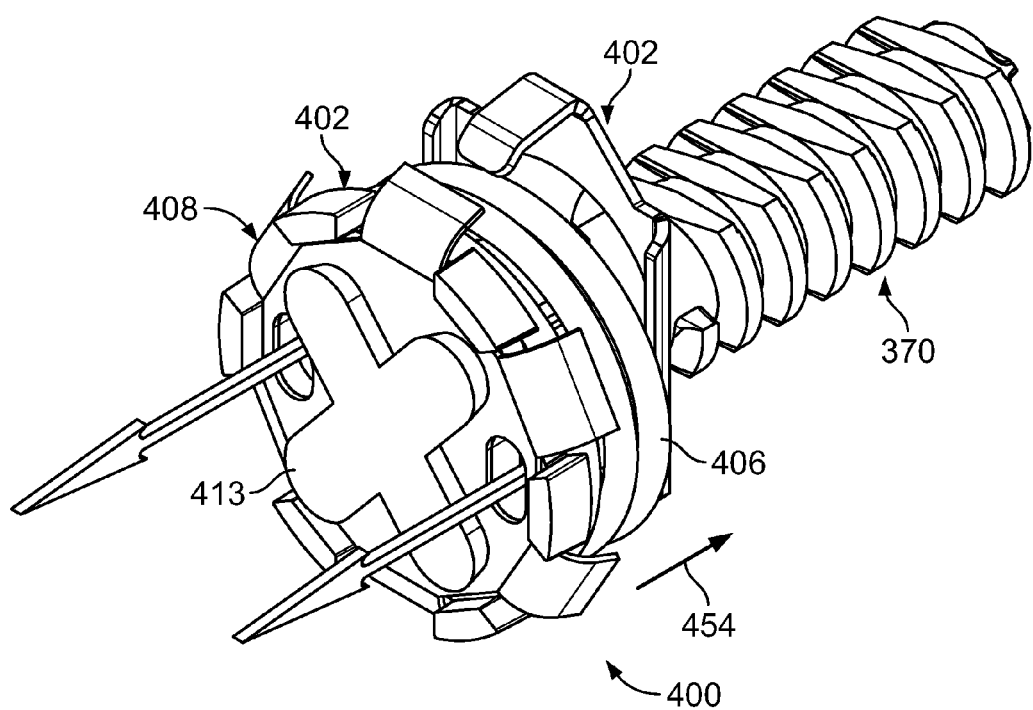
FIG. 5A is perspective view of the plunger engagement device of FIG. 4.
Figure 5B:
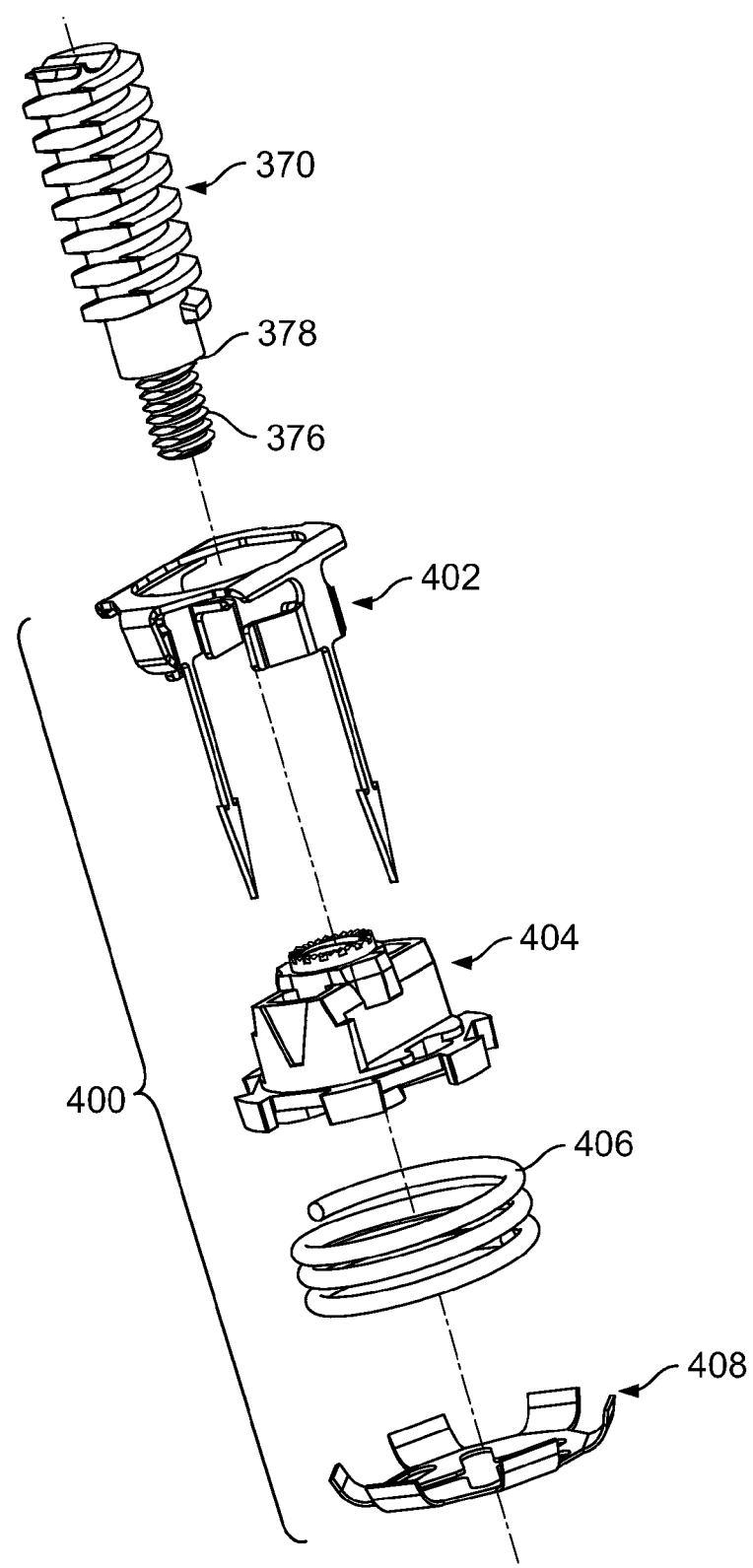
FIG. 5B is a perspective exploded view of the plunger engagement device of FIG. 4
Figure 6:
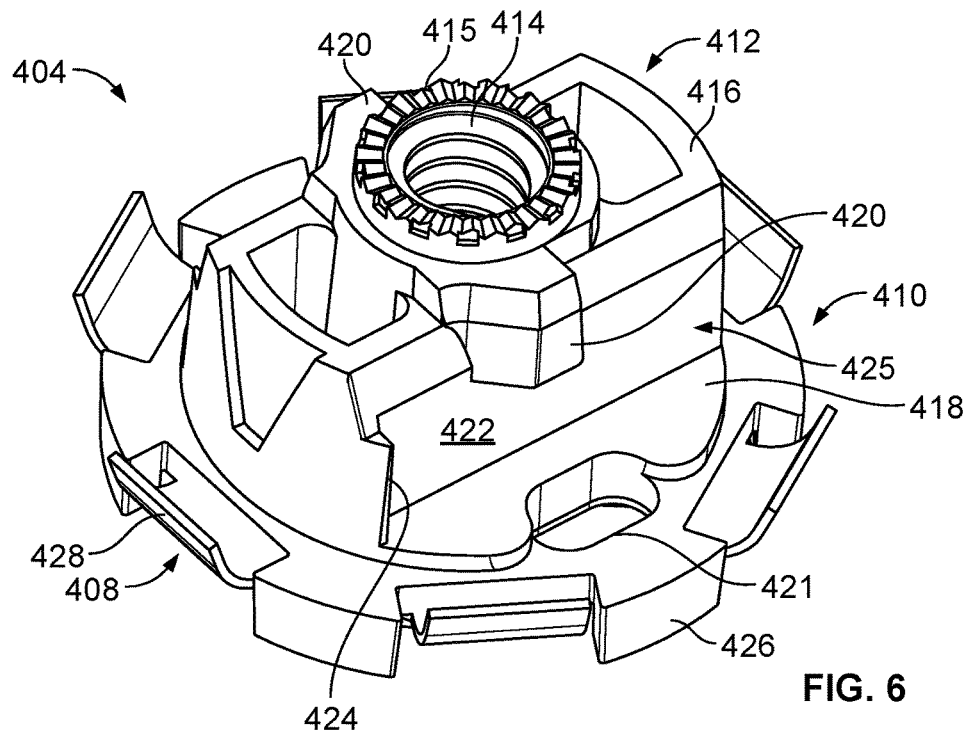
FIG. 6 is a perspective view of a piston hub and a spring hub of the plunger engagement device of FIG. 4.

As shown in FIGS. 5A and 5B, the plunger engagement device 400 includes a retention plate 402, a piston hub 404, a retention spring 406, and a spring hub 408. Referring to FIG. 6, the piston hub 404 includes a circular base 410, a central frame 412 upstanding from the base 410, and a pusher block 413 formed on an underside of the base 410 (opposite the frame 412 and facing the plunger 125). The pusher block 413 is provided with a substantially flat surface that contacts the rear face of the plunger 125 to press the plunger 125 through the fluid cartridge 120 as the piston rod 370 is driven forward by the drive wheel 360. The frame 412 includes a threaded bore 414, an oblong oval-shaped support structure 416, opposing platforms 418, and opposing arm members 420. Openings 421 are provided on either side of the support structure 416 and extend through the platforms 418 and the base 410 of the piston hub 404, as well as through the spring hub 408.

The bore 414 is shaped to receive a threaded forward end 376 of the piston rod 370 (FIG. 5B). With the forward end 376 of the piston rod 370 threadingly received by the bore 414, a radial shoulder 378 of the piston rod 370 abuts a load bearing rim 415 at the opening of the bore 414. During use, as the piston rod 370 is advanced forward by the drive wheel 360, the shoulder 378 of the piston rod 370 presses against the rim 415 of the piston hub 404 to urge the piston hub 404, and therefore the plunger 125, through fluid cartridge 120. Each of the two long sides of the oblong support structure 416 defines a side wall 422 and an end wall 424. The platforms 418 extend outward from a lower portion of the side walls 422, along the base 410. The arm members 420 extend outward from the bore 414, to overhang the respective platforms 418. Together, the side wall 422, the end wall 424, the platform 418, and the arm member 420 create a slot 425 for receiving a latch member 434 (FIG. 7) of the retention plate 402.

The base 410 radially surrounds the frame 412 to provide a flange including a plurality of radial spokes 426. The spokes 426 are spaced apart from one another and distributed circumferentially around the base 410. The spring hub 408 is attached to the undersurface the base 410 and includes a plurality of radial tabs 428 protruding through the spaces between neighboring spokes 426. In this embodiment, the piston hub 404 includes six spokes 426 and the spring hub 408 includes six tabs 428. However, other suitable configurations are also contemplated within the scope of this document. The tabs 428 of the spring hub 408 extend obliquely outward along a curved upslope to meet the inner wall of the fluid cartridge 120. The tabs 428 are both flexible and resilient, and therefore bear against the inner wall of the cartridge 120. Thus, the tabs 428 provide substantial frictional forces that resist movement of the spring hub 408 (and therefore the attached piston hub 404) rearward relative to the fluid cartridge 120. However, the curved upsloping shape and orientation of the tabs 428 causes the tabs 428 to flex inward when the spring hub 408 (and therefore the attached piston hub 404) is forced forward relative to the fluid cartridge 120 (e.g., in response a force provided by the piston rod 370, or the force 140).

Figure 7:
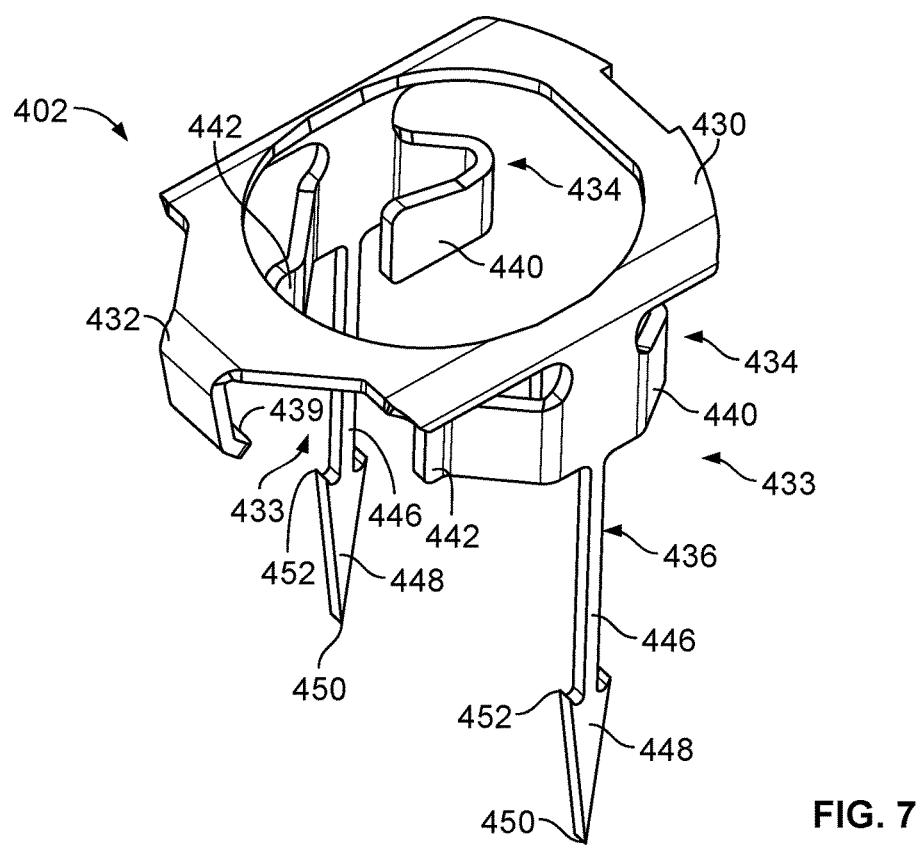
FIG. 7 is a perspective view of a retention plate of the plunger engagement device of FIG. 4.

Referring to FIG. 7, the retention plate 402 includes a chassis 430 supporting a trigger tab 432 and a pair of opposing struts 433. The retention plate 402 fits together with the piston hub 404 and the spring hub 408 (as shown in FIG. 5A). Accordingly, in this embodiment, the chassis 430 has an oblong shape approximating that of the support structure 416 of the piston hub 404, with a relatively large central opening 438 exposing the bore 414 of the piston hub 404 for engagement with the piston rod 370. The struts 433 extend longitudinally from the long sides of the oblong chassis 430, partially projecting through the openings 421 of the piston hub 404 and the spring hub 408. The trigger tab 432 extends longitudinally from one of the shorter ends of the chassis 430 in the same direction as the struts 433. In this embodiment, the trigger tab 432 includes an oblique inwardly facing lip 439.

Each of the struts 433 includes a latch member 434 and a penetration member 436. The latch member 434 includes a catch member 440 and a finger flange 442. With the retention plate 402 installed on the piston hub 404, the latch member 434 of each strut 433 is located in a respective slot 425 of the piston hub 404. In this position, the catch member 440 and the finger flange 442 are slidingly engaged with the side wall 422 and the platform 418 of the piston hub 404, with the finger flange 442 seated against the end wall 424 and the catch member 440 located beneath the arm member 420. Each of the penetration members 436 includes an elongated shank 446 projecting through a respective opening 421 of the piston hub 404 (and the spring hub 408) to terminate in a distal tip 448. As noted above, the penetration member 436 are configured (e.g., appropriately sized, shaped, and otherwise fabricated) to couple the plunger 125 to the piston rod 370 during operation of the pump device 100. The penetration members 436 may extend to a total length (including the shank 446 and the tip 448) that is slightly less than the axial length of the plunger 125. In such circumstances, the penetration members 436 do not penetrate through the front face (e.g., the "wet" face) of the plunger 125 (FIGS. 8A-C).

In this embodiment, each of the distal tips 448 of the respective penetration members 436 is provided in the form of an arrow shaped member including a pointed head 450 and opposing angled-cut retention barbs 452. The pointed head 450 of the tip 448 may facilitate penetration into the rear face of the plunger 125 (e.g., the "dry" face of the plunger 125 opposite the "wet" face). The retention barbs 452 of the tip 448 may enhance the engagement between the penetration member 436 and the plunger 125, thereby increasing a retention force that resists relative longitudinal movement between the plunger 125 and the penetration members 436.

It should be understood from the description herein that, in other embodiments, the penetration members 436 may have a different configuration. For example, in some embodiments, suitable penetration members may be provided in the form of pin inserts. Such penetration members can include a generally straight shank and pointed tip to facilitate penetration into the rear face of the plunger. In some embodiments, suitable penetration members can be provided in the form of radially curved blades. Such embodiments of the penetration members may include generally flat blade shanks that are curved about a longitudinal axis. In some embodiments, the retention barbs can be straight-cut portions. In some embodiments, the pointed head of at the tip of the penetration member can include one or more serrations or other retention features to increase the retention force. Penetration members with different configurations may provide varying amounts of retention force.

In some embodiments, the penetration members 436 can reduce the compliance of the plunger material and thereby increase the dosage accuracy. For example, the plunger 125 may comprise an elastomer material that exhibits flexibility and compliance when it is urged longitudinally relative to the inner wall of the fluid cartridge 120 (e.g., the center of the plunger is urged forward while the outer radial surfaces flex due to the frictional engagement with the inner wall of the fluid cartridge). Such compliance may create a level of unpredictability between the piston rod movement and the corresponding plunger movement. The penetration members 436 can pierce into the plunger 125 and thereby serve as generally rigid inserts that reduce the compliance exhibited by the plunger 125. In some circumstances, the penetration members 436 can serve as inserts that provide greater uniformity between the piston rod movement and the corresponding plunger movement. As such, the pump device 100 may have increased accuracy for the dosage of medicine that is dispensed in response to an incremental movement of the piston rod 370. In this embodiment, the retention plate 402 includes two penetration members 436 that are laterally offset from the center plunger 125, so as to pierce the rear face of the plunger 125 in an outer radial portion of the plunger 125 (e.g., a portion of the plunger that might otherwise be more compliant during advancement of the plunger 125 inside the fluid cartridge 120).

Referring back to FIGS. 5A and 5B, the retention spring 406 is sandwiched between the retention plate 402 and the piston hub 404. In this embodiment, the retentions spring 406 is a coiled compression spring surrounding the support structure 416 (FIG. 5A). The retention spring 406 bears against the base 410 of the piston hub 404 at one end, and bears against the chassis 430 of the retention plate 402 at the opposing end. Thus, the retention spring 406 urges the retention plate 402 away from the piston hub 404 with a spring force 454. The magnitude of the spring force 454 is based on the configuration of the retention spring 406 (e.g., the stiffness and compression displacement of the retention spring 406). As described below, in a deactivated condition (FIG. 8A), the retention plate 402 is held, in resistance of the spring force 454, in a fixed position relative to the piston hub 404 by the arm members 420 of the piston hub 404 interacting with the catch members 440 of the retention plate 402. In the activated condition (FIG. 8B), when the catch members 440 are disengaged from the arm members 420, the spring force 454 is permitted to move the retention plate 402.

Referring to FIGS. 8A-C, in operation, the plunger engagement device 400 can be secured to the plunger 125 and reduce or eliminate a gap 405 (or relative motion that might otherwise cause a gap) between the plunger 125 and the piston rod 370. As previously described in connection with FIG. 1, a longitudinal force 140 may be applied to the fluid cartridge 120, for example, during insertion of the fluid cartridge 120 into the cavity 116 (applied via the user's finger's) and/or during engagement of the cap device 130 to the pump housing 110. This longitudinal force 140 is used to urge the fluid cartridge 120 (and the plunger 125 therein) toward the penetration members 436 of the plunger engagement device 400. As the plunger 125 continues its motion toward the pusher block 413 in response to the longitudinal force 140, the penetration members 436 can pierce into the rear face of the plunger 125. The retention spring 406 remains in the deactivated condition.

As shown in FIG. 8A, the fluid cartridge 120 moves under the longitudinal force 140 with some relatively minor resistance caused by the penetration members 436 moving through the material of the plunger 125) until the outer rim 456 of the fluid cartridge 120 encounters the lip 439 of the trigger tab 432. As shown in FIG. 8B, the inward slope of the lip 439 causes the chassis 430 of the retention plate 402 to be pushed across the fluid cartridge 120 (relative to the piston hub 404) as a result of the chassis 430 sliding relative to the rear rim 456 of the cartridge 120 (due to the longitudinal force 140). The crosswise movement 140' of the chassis 430 activates the retention spring 406. In this embodiment, the crosswise movement 140' of the chassis 430 causes the penetration members 436 of each strut 433 to move within the plunger 125. For example, the tips 448 may rotate and/or the shanks 446 may flex or bend within the plunger 125. Further, the crosswise movement 140' of the chassis 430 causes the catch member 440 of each strut 433 to slide along the slot 425 of the piston hub 404 to disengage from the arm embers 420 of the piston hub 404, thereby releasing the retention spring 406.

As shown in FIG. 8C, once released, the retention spring 406 applies the spring bias force 454 that urges the retention plate 402 longitudinally away from the piston hub 404 until the plunger 125, carried by the penetration members 436, is pressed into abutment the pusher block 413 of the piston hub (FIG. 8C). Thus, the retention spring 406 biases the plunger 125 against the forward face of the pusher block 413, thereby eliminating or otherwise reducing the gap 405 to a negligible amount and thereafter retaining the plunger 125 in a predictable position relative to the piston rod 370 during operation of the pump device 100. Further, the longitudinal movement of the retention plate 402 allows the penetration members 436 to straighten within the plunger 125 to hold the chassis 430 in a position where the trigger tab 432 clears the rim 456 and side wall of the fluid cartridge 120.

Figure 9:
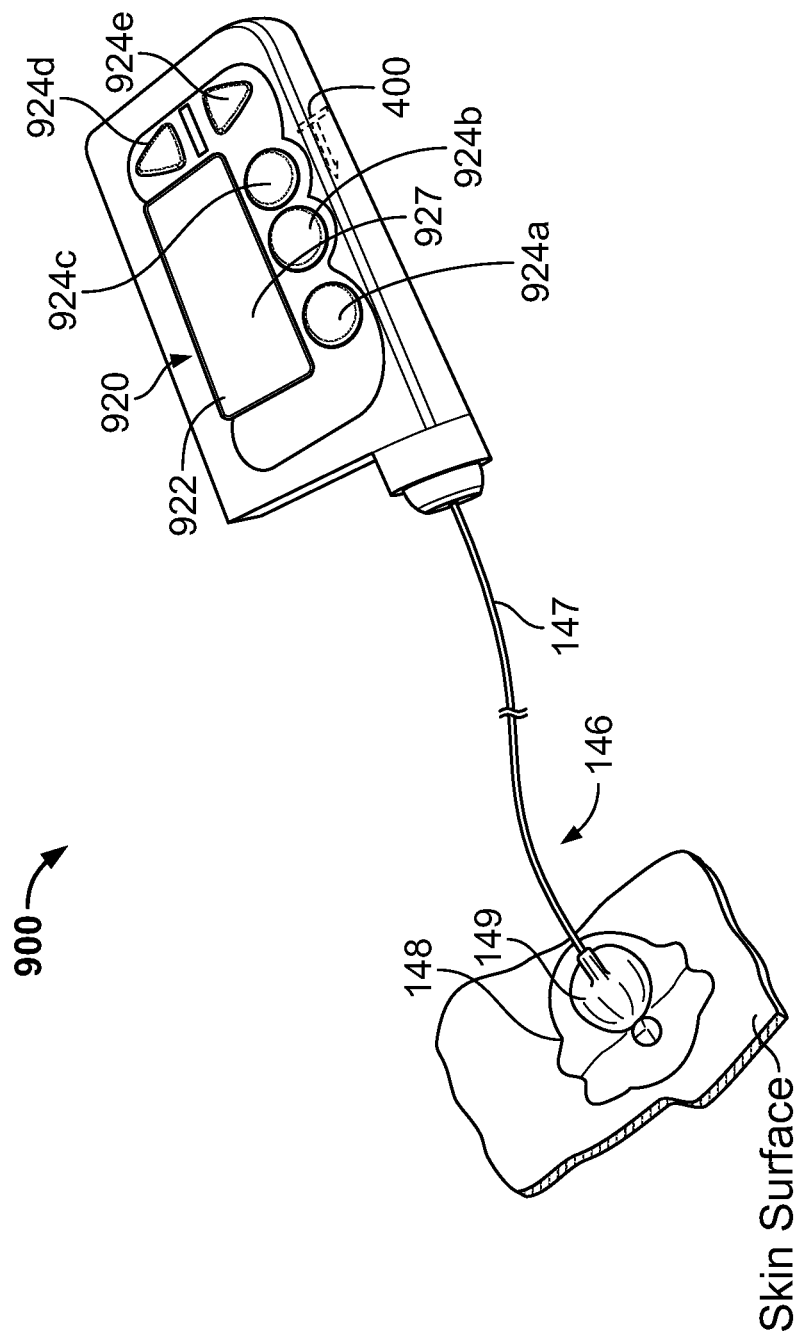
FIG. 9 is a perspective view of an alternative infusion pump system in accordance with some embodiments.

Referring now to FIG. 9, some embodiments of a portable infusion pump system 900 having a plunger engagement device 975 can employ a reusable pump apparatus (rather than a disposable pump device as previously described). In such circumstances, the infusion pump system 900 may comprise a reusable device that houses the control circuitry and the pump drive system within a single housing construct. In the particular embodiment depicted in FIG. 9, the pump system 900 comprises a reusable pump device that houses both the controller circuitry and the pump drive system. Similar to previously described embodiments, the pump system 900 can include a housing that defines a cavity in which a fluid cartridge can be received (not shown in FIG. 9; refer for example to fluid cartridge 120 in FIG. 1). For example, the pump system 900 can be adapted to receive a fluid cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 900 on the user's skin under clothing or in the user's pocket while receiving the medicine dispensed through the infusion set 146.

Similar to previously described embodiments of the plunger engagement device 400 (FIGS. 8A-8C), the plunger engagement device 975 of the infusion pump system 900 may include a retention spring (not shown) that, once activated biases the plunger of the fluid cartridge towards a piston rod 370 of the drive system to increase dosage accuracy.

Still referring to FIG. 9, the user interface 920 of the pump system 900 includes a display device 922 and one or more user-selectable buttons 924a-e. The display device 922 can include an active area in which numerals, text, symbols, images, or a combination thereof can be displayed. The display device 922 can be used to communicate a number of settings or menu options for the infusion pump system 900. For example, the display device 922 can be used to communicate medicinal delivery information 927, such as the basal delivery rate, a bolus dosage, a historical record of medicine delivered, the amount of medicine remaining in the fluid cartridge, or the like. In another example, the display device 922 can be used to communicate time and date information, which can be used by the user to determine dosage schedules, bolus delivery times, meal times, or the like.

Accordingly, the user may press one or more of the buttons 924a, 924b, 924c, 924d, and 924e to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like). Also, the user can adjust the settings or otherwise program the pump system 900 by pressing one or more buttons 924a, 924b, 924c, 924d, and 924e of the user interface 920. Thus, the user can contemporaneously monitor the operation of the pump system 900 from the same user interface 920.

A number of embodiments of the invention have been described. Nevertheless, it will be understood that various modifications may be made without departing from the scope of the invention. Accordingly, other embodiments are within the scope of the following claims.

What is claimed is:

1. A portable infusion pump system, comprising:
   a pump housing that defines a space to receive a medicine cartridge; and
   a drive system to dispense medicine from the medicine cartridge when the medicine cartridge is received by the pump housing, the drive system comprising: a piston rod configured to forwardly advance toward the medicine cartridge when the medicine cartridge is received by the pump housing, and a plunger engagement device coupled to the piston rod,
   wherein the plunger engagement device comprises at least one penetration member to couple the drive system to a plunger of the medicine cartridge, and a spring adjustable from a deactivated condition to an activated condition in which a spring force of the spring biases the plunger towards the piston rod in a direction opposite of a forward direction of the piston rod when the piston rod is forwardly advanced toward the medicine cartridge when the medicine cartridge is received by the pump housing.

2. The portable infusion pump system of claim 1, wherein the plunger engagement device further comprises a retention plate comprising a chassis seated against the spring causing the retention plate to move as the spring expands during adjustment from the deactivated condition to the activated condition, wherein the chassis is fixedly coupled to the at least one penetration member, and wherein the retention plate further comprises an aperture, the piston rod extending through the aperture of the retention plate.

3. The portable infusion pump system of claim 1, wherein the plunger engagement device further comprises a trigger tab engageable with a portion of the medicine cartridge to adjust the spring from the deactivated condition to the activated condition in response to a longitudinal force applied to the medicine cartridge.

4. The portable infusion pump system of claim 3, further comprising a cap device that engages the pump housing to retain the medicine cartridge therein when the medicine cartridge is received by the pump housing, wherein when the cap device engages the pump housing, the cap device acts upon the medicine cartridge to provide the longitudinal force.

5. The portable infusion pump system of claim 4, wherein the cap device comprises a needle device that penetrates an output portion of the medicine cartridge when the cap device engages the pump housing.

6. The portable infusion pump system of claim 3, wherein the trigger tab extends from a chassis supporting the at least one penetration member, and wherein the trigger tab comprises an oblique inwardly facing lip bearing against the portion of the medicine cartridge to move the chassis across the medicine cartridge in response to the longitudinal force.

7. The portable infusion pump system of claim 1, wherein the plunger engagement device further comprises a piston hub fixedly coupled to the piston rod, the piston hub comprising a base supporting the spring and a pusher block contacting the plunger when the spring is in the activated condition.

8. The portable infusion pump system of claim 1, wherein the plunger engagement device further comprises a spring hub comprising a plurality of radial tabs obliquely outward along a curved upslope to meet an inner wall of the medicine cartridge when the medicine cartridge is received by the pump housing.

9. The portable infusion pump system of claim 1, wherein the at least one penetration member comprises a pointed head and opposing retention barbs.

10. The portable infusion pump system of claim 1, wherein the plunger engagement device further comprises a catch member engageable with a portion of a piston hub supporting the spring, and wherein the catch member is releasable from the portion of the piston hub to adjust the spring from the deactivated condition to the activated condition.

11. The portable infusion pump system of claim 1, further comprising a controller device removably attachable to the pump housing so as to electrically connect with a pump device comprising the pump housing and the drive system, wherein the controller device houses control circuitry configured to communicate with the drive system positioned in the pump housing to control dispensation of the medicine from the pump device.

12. A portable infusion pump system, comprising:
a pump housing that defines a space to receive a medicine cartridge;
a drive system to dispense medicine from the medicine cartridge when the medicine cartridge is received by the pump housing, the drive system comprising: a piston rod configured to forwardly advance toward the medicine cartridge when the medicine cartridge is received by the pump housing, and a plunger engagement device coupled to the piston rod; and
a controller device removably attachable to the pump housing so as to electrically connect with a pump device comprising the pump housing and the drive system, wherein the controller device houses control circuitry configured to communicate with the drive system positioned in the pump housing to control dispensation of the medicine from the pump device,
wherein the plunger engagement device comprises: a piston hub coupled to the piston rod, a retention plate having an aperture that encompasses a portion of the piston rod, at least one penetration member supported by the retention plate to couple the drive system to a plunger of the medicine cartridge, and a spring seated between the piston hub and the retention plate, and
wherein the spring is adjustable from a deactivated condition to an activated condition in which a spring force of the spring biases the retention plate away from the piston hub to pull the plunger against a surface of the piston hub.

13. The portable infusion pump system of claim 12, wherein the retention plate comprises a trigger tab defining an oblique inwardly facing lip bearing against a portion of the medicine cartridge to adjust the spring from the deactivated condition to the activated condition in response to a longitudinal force applied to the medicine cartridge.

14. The portable infusion pump system of claim 13, further comprising a cap device that engages the pump housing to retain the medicine cartridge therein when the medicine cartridge is received by the pump housing,
wherein when the cap device engages the pump housing, the cap device acts upon the medicine cartridge to provide the longitudinal force, and
wherein the cap device comprises a needle device that penetrates an output portion of the medicine cartridge when the cap device engages the pump housing.

15. The portable infusion pump system of claim 12, wherein the plunger engagement device further comprises a spring hub attached to a base of the piston hub, the spring hub comprising a plurality of radial tabs obliquely outward along a curved upslope to meet an inner wall of the medicine cartridge when the medicine cartridge is received by the pump housing.

16. The portable infusion pump system of claim 12, wherein the retention plate comprises a catch member engageable with a portion of the piston hub to hold the spring in the deactivated condition, and wherein the catch member is releasable from the portion of the piston hub to release the spring from the deactivated condition to the activated condition.

17. A portable infusion pump system, comprising:
a pump housing that defines a space to receive a medicine cartridge; and
a drive system to dispense medicine from the medicine cartridge when the medicine cartridge is received by the pump housing, the drive system comprising: a piston rod configured to forwardly advance toward the medicine cartridge when the medicine cartridge is received by the pump housing, and a plunger engagement device coupled to the piston rod,
wherein the plunger engagement device comprises at least one means for penetrating a plunger of the medicine cartridge, and a means for biasing the plunger towards the piston rod in a direction opposite of a forward direction of the piston rod when the piston rod is forwardly advanced toward the medicine cartridge when the medicine cartridge is received by the pump housing by adjusting from a deactivated condition to an activated condition.

18. A method of operating an infusion pump device, comprising:
receiving a medicine cartridge in an internal space of a housing of a pump device, wherein a plunger engagement device is positioned in the internal space;
penetrating a plunger of the medicine cartridge with at least one penetration member of the plunger engagement device; and
after penetrating the plunger with said at least one penetration member, applying a spring bias of a spring to the plunger to bias the plunger towards a piston rod of a drive system of the pump device, wherein the spring biases the plunger towards the piston rod in a direction opposite of a forward direction of the piston rod when the piston rod is forwardly advanced toward the medicine cartridge when the medicine cartridge is received by the pump housing.

19. The method of claim 18, wherein the steps of penetrating the plunger and applying the spring bias to the plunger comprise applying a longitudinal force to the medicine cartridge.

20. The method of claim 19, wherein the step of applying the spring bias to the plunger further comprises adjusting the spring from a deactivated condition to an activated condition by applying the longitudinal force.

21. The method of claim 19, wherein the step of applying the longitudinal force comprises engaging a cap device with the housing of the pump device to retain the medicine cartridge in the internal space.

* * * * *